United States Patent
Han et al.

(10) Patent No.: US 9,999,899 B2
(45) Date of Patent: Jun. 19, 2018

(54) CONTROLLED EXPOSURE OF IN-VIVO SENSORS

(71) Applicant: INTERNATIONAL BUSINESS MACHINES CORPORATION, Armonk, NY (US)

(72) Inventors: Shu-Jen Han, Cortlandt Manor, NY (US); Bharat Kumar, Tarrytown, NY (US); George S. Tulevski, Croton-on-Hudson, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days. days.

(21) Appl. No.: 15/340,180

(22) Filed: Nov. 1, 2016

(65) Prior Publication Data
US 2018/0117624 A1    May 3, 2018

(51) Int. Cl.
*A61B 5/00*      (2006.01)
*B05D 1/00*      (2006.01)
*A61B 5/145*     (2006.01)
*B05D 7/00*      (2006.01)
*B05D 3/04*      (2006.01)

(52) U.S. Cl.
CPC ............ *B05D 1/005* (2013.01); *A61B 5/0004* (2013.01); *A61B 5/14503* (2013.01); *A61B 5/14532* (2013.01); *A61B 5/14542* (2013.01); *A61B 5/14546* (2013.01); *B05D 3/0413* (2013.01); *B05D 7/5483* (2013.01)

(58) Field of Classification Search
CPC . A61B 5/0059; A61B 5/1455; A61B 5/14551; A61B 5/14532; A61B 5/14546; A61B 5/1459; A61B 5/0004; A61B 5/14503; A61B 5/14542
See application file for complete search history.

(56) References Cited

U.S. PATENT DOCUMENTS

| | | | |
|---|---|---|---|
| 4,660,721 A * | 4/1987 | Mykleby | A61L 2/26 206/438 |
| 4,846,844 A | 7/1989 | De Leon et al. | |
| 5,217,493 A | 6/1993 | Raad et al. | |
| 6,119,028 A * | 9/2000 | Schulman | A61B 5/14532 600/345 |
| 6,330,464 B1 * | 12/2001 | Colvin, Jr. | A61B 5/14532 600/316 |
| 7,550,005 B2 | 6/2009 | Bates et al. | |
| 7,572,298 B2 | 8/2009 | Roller et al. | |
| 7,608,581 B2 | 10/2009 | Hamilton et al. | |

(Continued)

FOREIGN PATENT DOCUMENTS

EP    1784122 A2    5/2007
WO    2015200723 A1    12/2015

*Primary Examiner* — Eric Winakur
*Assistant Examiner* — Chu Chuan (JJ) Liu
(74) *Attorney, Agent, or Firm* — Cantor Colburn LLP; Vazken Alexanian

(57) ABSTRACT

A method of protecting an in-vivo sensor includes forming a sensing surface on a surface of the in-vivo sensor, the sensing surface including a functionalized monolayer that will bind to an analyte of interest; and coating the sensing surface of the sensor with a bioabsorbable polymeric coating including a bioabsorbable polymer; wherein the bioabsorbable polymeric coating is configured to protect the in-vivo sensor until needed for implantation.

11 Claims, 12 Drawing Sheets

(56) References Cited

U.S. PATENT DOCUMENTS

| | | | |
|---|---|---|---|
| 8,315,700 B2 | 11/2012 | Citron et al. | |
| 8,571,659 B2* | 10/2013 | Kane | A61B 5/14546 607/22 |
| 8,696,564 B2 | 4/2014 | Chavan et al. | |
| 8,900,619 B2 | 12/2014 | Ranade et al. | |
| 9,204,830 B2 | 12/2015 | Zand et al. | |
| 9,381,281 B2 | 7/2016 | Lerner et al. | |
| 2002/0128234 A1* | 9/2002 | Hubbell | A61B 5/1459 514/100 |
| 2003/0073961 A1* | 4/2003 | Happ | A61L 31/10 604/274 |
| 2004/0023317 A1* | 2/2004 | Motamedi | A61B 5/14532 435/14 |
| 2005/0272989 A1* | 12/2005 | Shah | A61B 5/14532 600/345 |
| 2009/0221891 A1 | 9/2009 | Yu et al. | |
| 2010/0168808 A1 | 7/2010 | Citron | |
| 2010/0298674 A1* | 11/2010 | Colvin, Jr. | A61B 5/14532 600/316 |
| 2015/0257787 A1 | 9/2015 | Haigh et al. | |

* cited by examiner

CONTROLLED EXPOSURE OF IN-VIVO SENSORS

BACKGROUND

Embodiments of the present invention relate to sensors, and more specifically, to controlled in-vivo sensors.

In-vivo chemical sensors are attractive areas of research in medical device manufacturing and development. Generally, fabrication of such chemical sensors includes coating a surface of a sensor with a marker, such as a protein, aptamer, deoxyribonucleic acid (DNA) segment, or some other biomarker. The marker then attaches to the desired analyte of interest, for example, a protein of interest, and the signal is then transduced with a device, such as a transistor. The sensors can include additional "non-fouling compounds" that prevent the nonspecific binding of undesired proteins.

SUMMARY

According to an embodiment, a method of protecting an in-vivo sensor includes forming a sensing surface on a surface of the in-vivo sensor, the sensing surface including a functionalized monolayer that will bind to an analyte of interest; and coating the sensing surface of the sensor with a bioabsorbable polymeric coating including a bioabsorbable polymer; wherein the bioabsorbable polymeric coating is configured to protect the in-vivo sensor until needed for implantation.

According to another embodiment, a method of fabricating a controlled in-vivo sensor includes forming a sensing surface on a surface of a sensor, the sensing surface including a functionalized monolayer that will bind to an analyte of interest; and coating the sensing surface of the sensor with a bioabsorbable polymeric coating including a bioabsorbable polymer; wherein the controlled in-vivo sensor is configured to be implantable into a living animal, and the bioabsorbable polymeric coating is configured to desorb after being implanted and exposed to a biological environment.

Yet, according to another embodiment, a controlled in-vivo sensor includes a sensing surface including a functionalized monolayer configured to bind to an analyte of interest; and a bioabsorbable polymeric coating including a bioabsorbable polymer configured to protect the sensing surface until the controlled in-vivo sensor is implanted and exposed to a biological environment of a living animal.

BRIEF DESCRIPTION OF THE DRAWINGS

The subject matter which is regarded as embodiments of the invention is particularly pointed out and distinctly claimed in the claims at the conclusion of the specification. The foregoing and other features, and advantages of the embodiments of the invention are apparent from the following detailed description taken in conjunction with the accompanying drawings in which:

FIGS. 1-3 illustrate exemplary methods of controlled in-vivo sensing according to embodiments, in which:

FIG. 1 is a cross-sectional side view after forming a sensing surface on a surface of a sensor;

FIG. 2 is a cross-sectional side view after disposing a bioabsorbable polymer on the sensing surface;

FIG. 3 is a cross-sectional side view of the sensor after being implanted into a living animal for a period of time;

DETAILED DESCRIPTION

Figure 1:
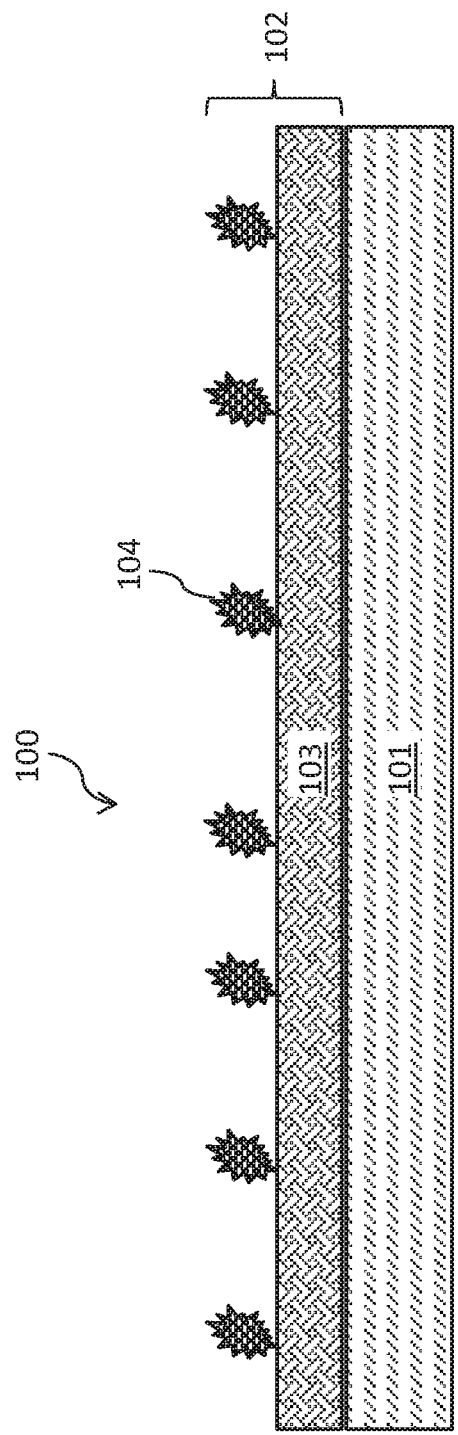

Embodiments of the present invention are described herein with reference to the related drawings. Alternative embodiments can be devised without departing from the scope of this invention. It is noted that various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. As an example of an indirect positional relationship, references in the present description to forming layer "A" over layer "B" include situations in which one or more intermediate layers (e.g., layer "C") is between layer "A" and layer "B" as long as the relevant characteristics and functionalities of layer "A" and layer "B" are not substantially changed by the intermediate layer(s).

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include an indirect "connection" and a direct "connection."

References in the specification to "one embodiment," "an embodiment," "an example embodiment," etc., indicate that the embodiment described can include a particular feature, structure, or characteristic, but every embodiment may or may not include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper," "lower," "right," "left," "vertical," "horizontal," "top," "bottom," and derivatives thereof shall relate to the described structures and methods, as oriented in the drawing figures. The terms "overlying," "atop," "on top," "positioned on" or "positioned atop" mean that a first element, such as a first structure, is present on a second element, such as a second structure, wherein intervening elements such as an interface structure can be present between the first element and the second element. The term "direct contact" means that a first element, such as a first structure, and a second element, such as a second structure, are connected without any intermediary conducting, insulating or semiconductor layers at the interface of the two elements. It should be noted that the term "selective to," such as, for example, "a first element selective to a second element," means that the first element can be etched and the second element can act as an etch stop.

As used herein, the terms "about," "substantially," "approximately," and variations thereof are intended to include the degree of error associated with measurement of the particular quantity based upon the equipment available at the time of filing the application. For example, "about" can include a range of ±8% or 5%, or 2% of a given value.

For the sake of brevity, conventional techniques related to semiconductor device and integrated circuit (IC) fabrication may or may not be described in detail herein. Moreover, the various tasks and process steps described herein can be incorporated into a more comprehensive procedure or process having additional steps or functionality not described in detail herein. In particular, various steps in the manufacture of semiconductor devices and semiconductor-based ICs are well known and so, in the interest of brevity, many conventional steps will only be mentioned briefly herein or will be omitted entirely without providing the well-known process details.

Turning now to a description of technologies that are more specifically relevant to aspects of the present invention, embodiments herein are directed to in-vivo sensing, as mentioned above. Prior to implantation into the body of a living animal, the in-vivo sensor is initially sterilized to prevent infection. The sensors have finite lifetimes, for example hours or days, after which time the sensor can become non-functional, whether or not they are exposed to a biological environment.

There are two challenges that can be associated with such in-vivo sensors. First, in-vivo sensors can be challenging to sterilize because thin organic films arranged on their surfaces can be unstable under sterilization conditions. Second, although "non-fouling" coatings can be incorporated into the sensors to delay deterioration of a functional sensor, the sensor surfaces can nonetheless foul over time.

Accordingly, described herein are methods of fabricating in-vivo sensors with a bioabsorbable coating that is configured to desorb over a predetermined and controlled period of time. The bioabsorbable coating allows for the introduction of new sensors at some time after implantation. The bioabsorbable coating also allows for sterilization, as the coating protects the organic films arranged beneath. According to embodiments, the bioabsorbable coating thickness and composition are controlled to expose the sensor to the in-vivo environment at controlled times after implantation.

Figure 2:
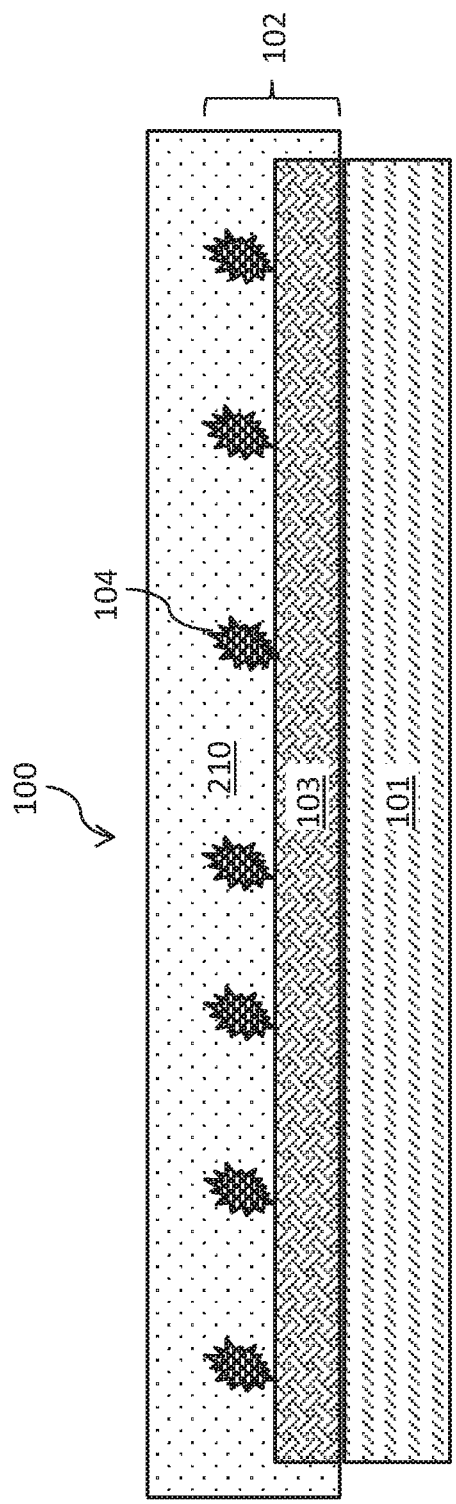

Turning now to the figures, FIGS. 1 and 2 illustrate methods of fabricating an in-vivo sensor 100. Sensor 100 includes a substrate 101 with a sensing surface 102 arranged on the substrate 101. In FIG. 1, a sensing surface 102 is formed on substrate 101. The substrate 101 can include, but is not limited to, metals, metal alloys, semiconductors, insulators, or a combination thereof. In an exemplary embodiment, the substrate 101 includes a gold film.

The sensing surface 102 includes a monolayer 103 arranged on a surface of the substrate 101. The monolayer 103 includes a functional group that is bound to the substrate 101. For example, when the substrate 101 is a gold film, the monolayer 103 can include a thiolated end group that bonds to the substrate 101. The monolayer 103 includes a polymer that extends from a surface of the substrate 101 to a chemical moiety 104.

The monolayer 103 can include any polymer or copolymer. The monolayer 103 can include hydrophobic polymers, such as polysiloxane, and/or hydrophilic polymers, such as polyuria and polyurethane. The monolayer 103 can include a blend of two or more polymers, each of which can include a combination of two or more polymers with different characteristics, including combinations of hydrophobic and hydrophilic polymers. In embodiments, the monolayer 103 includes polyethylene glycol (PEG). In other embodiments, the hydrophilic polymer includes a copolymer of polypropylene glycol and PEG.

The monolayer 103 is functionalized with chemical moiety 104. Chemical moiety 104 can be, but is not limited to, a protein, an antibody, an aptamer, a DNA segment, an RNA segment, a chemical compound, or a combination thereof. The chemical moiety 104 extends from the surface of the monolayer 103. The chemical moiety 104 can be any compound or molecule that can attach to the monolayer 103 and bond or interact with an analyte of interest once introduced into the body of a living animal.

The monolayer 103 functionalized with the chemical moiety 104 forms a thin organic film on a surface of the substrate 101. The monolayer 103 can have a thickness that generally varies and is not intended to be limited. In some embodiments, the monolayer 103 has a thickness in a range from about 0.5 to about 50 nm. In other embodiments, the monolayer 103 has a thickness in a range from about 10 to about 15 nm. Yet, in other embodiments, the monolayer 103 has a thickness outside of these ranges.

The sensor 100 can be any type of implantable sensor. The sensor 100 can be, for example, a chemical or biochemical sensor. The sensor 100 is configured to be implanted in a living animal (such as a living human). The sensor 100 can be configured for detection or continuous monitoring of an analyte of interest, such as glucose, oxygen, cardiac markers, low density lipoprotein, high density lipoprotein, or triglycerides. The sensor 100 can be configured to monitor for pathogen, such as for example, bacteria (e.g., methicillin resistant *staphylococcus aureus* (MRSA)) or viruses.

FIG. 2 is a cross-sectional side view after disposing a bioabsorbable polymer layer 210 on the sensing surface 102. The bioabsorbable polymer layer 210 is a coating that includes a bioabsorbable polymer. The bioabsorbable polymer layer 210 covers the sensing surface 102 and protects the sensing surface 102 during subsequent sterilization prior to implantation in a living animal. The bioabsorbable polymer layer 210 protects the thin organic films of the functionalized monolayer 103 from the high temperature and pressure of the sterilization conditions.

The thickness of the bioabsorable polymer layer 210 is not intended to be limited and can be tailored as desired. The bioabsorbable polymer layer 210 compositions and thickness can be tailored and controlled so that they desorb over time after being implanted in a living animal. Such control allows for the "introduction" of new sensors after a given time following initial implantation. The sensor 100 can then be exposed to the biological environment after implantation at controlled times.

In some embodiments, the thickness of the bioabsorbable polymer layer 210 is in a range from about 50 to about 1000 nm. In other embodiments, the thickness of the bioabsorbable polymer layer 210 is in a range from about 200 to about 300 nm.

The composition of the bioabsorbable polymer layer 210 can also be tailored as desired and is not intended to be limited. The bioabsorbable polymer of the layer 210 can include a bioabsorbable polymer. The polymer can include, but is not limited to, lactic acid, glycolic acid, glucose, polytrimethylene carbonate, collagen, laminin, hydroxyapatite, hyaluronan, and/or amino acids. In some embodiments, the polymer can include one or more linear polyesters such as, for example, polycaprolactone, poly-ester-ethers (such as polydioxanone), polyamino acids (such as poly-glutamate, poly-lysine, poly-leucine), poly-anhydrides (such as poly-sebacic acid), including derivatives, copolymers, and any combination thereof. The polymer can be a cross-linking polymer in some embodiments. In embodiments, the polymer is poly lactic acid.

The bioabsorbable polymer layer 210 covers the sensing surface 102 and can be deposited by any methods, which depend on the composition and desired thickness of the layer itself. In some embodiments, the bioabsorbable polymer layer 210 can be deposited by spin coating onto the sensing surface 102 of the sensor 100.

For simplicity, only a cut away portion of the sensor 100 is being shown. The size, shape, and dimensions of the sensor 100 can generally vary and depends on the particular application, for example, where the sensor will be implanted and the desired sensing function. Therefore, the sensor 100 can have any desired size, shape, and dimensions.

Once the sensor 100 is formed with the bioabsorbable polymer layer 210, the sensor 100 is sterilized. The sensor 100 can be sterilized under conditions suitable to render the sensor 100 sterile. The sensor 100 can be sterilized, for example, under elevated temperature and high pressure conditions. The sensor 100 can be sterilized under high pressure saturated steam at high temperatures. The sensor 100 can be sterilized using industrial instrumentation, such as an autoclave machine. The composition and thickness of the bioabsorbable polymer layer 210 is controlled such that the sensor 100 can withstand the sterilization conditions necessary to sterilize the sensor 100 before being implanted into the living animal.

Although non-fouling compounds can be generally incorporated in implantable sensors to prevent non-specific binding of undesired analytes, even non-fouling compounds foul over time. Fouling, or deterioration of the non-fouling compounds over time, can result in non-specific binding of undesired analytes to the sensor. The non-fouling compounds also cannot protect the thin organic layers of the sensor during sterilization.

Figure 3:
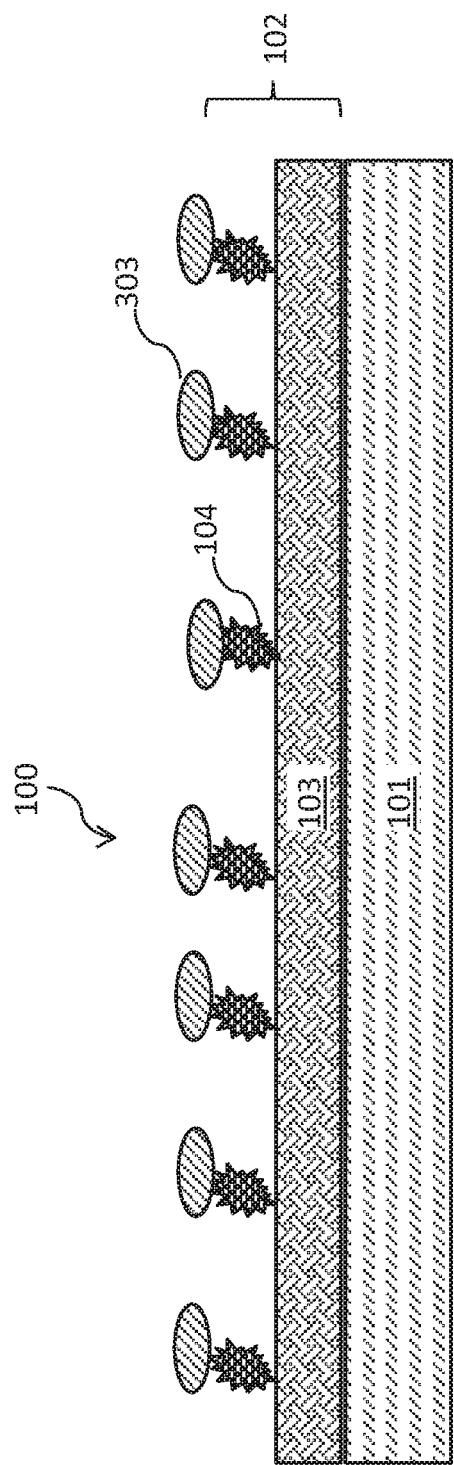

FIG. 3 is a cross-sectional side view of the sensor 100 after being implanted into a living animal for a period of time. The sensor 100 can be implanted into a living animal's arm, wrist, leg, abdomen, peritoneum, or other region suitable for sensor implantation. The sensor 100 can be implanted beneath the skin, such as in the subcutaneous or peritoneal tissue. The living animal can be a human or any other living animal, such as a mouse or rabbit.

After being implanted in the living animal, the bioabsorbable polymer layer 210 desorbs (dissolves or is at least partially removed from the surface of the sensor) over a period of time. Because the thickness and composition of the bioabsorbable polymer layer 210 can be tailored and controlled to desorb over a known and controlled period of time, the sensor 100 with the functionalized monolayer 103 (sensing surface 102) is exposed to the biological environment to be sensed at a controlled period of time.

Once a sensor without any protection is implanted in a living animal and exposed to the biological environment of the living animal, the sensor will eventually foul, or deteriorate. Even an unexposed sensor, before implantation, will eventually foul or deteriorate over time.

The bioabsorbable polymer layer 210, however, will slowly desorb or dissolve over a controlled period of time to expose the sensing surface 102 of the sensor to the biological environment. Similar to dissolvable sutures, for example, the bioabsorbable polymer layer 210 will dissolve or be removed to expose the sensing surface 102 after a known period time. The bioabsorable polymer layer 210 allows for exposure of a "new" sensor over a given and controlled time period. Thus the bioabsorbable polymer layer 210 provides a time-released biosensor. In embodiments, different sensors can be arranged as layers of different thicknesses or arranged side-by-side. The thickness and/or composition of each sensor can be adjusted to expose the sensors at different times.

Once the sensing surface 102 of the sensor 100 is exposed, the chemical moiety 104 interacts with or bonds to the analyte of interest 303. The analyte of interest 303 can be, but is not limited to, amino acids, proteins, peptides, sugars, carbohydrates, gas molecules, primary metabolites, secondary metabolites, lipids, nucleotides or nucleic acids, microbes, viruses, hormones, hydrocarbons, vitamins, amides, amines, glycosides, or any combination thereof. The analyte of interest 303 can be any natural biomolecule or biological byproduct formed in a living animal or found in a living animal. After the sensor binds to the analyte of interest, the signal is then transduced with a device, such as a transistor.

Figure 4A:
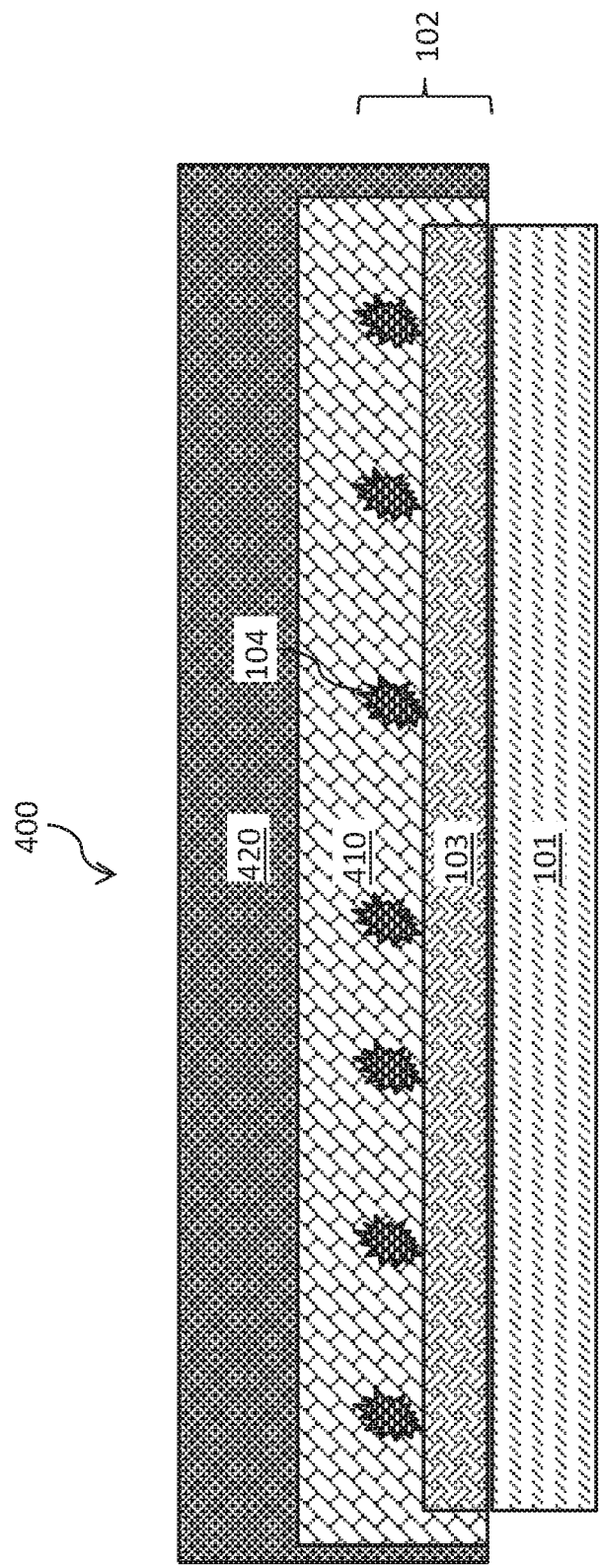
FIG. 4A is a cross-sectional side view of a controlled in-vivo sensor according to embodiments.

FIG. 4A is a cross-sectional side view of a controlled in-vivo sensor 400 according to embodiments. A non-fouling coating 410 is applied to the sensing surface 102 of the sensor 400. The non-fouling coating 410 provides some protection to the thin organic film of the sensor 400 and prevents non-specific binding of undesired analytes.

Examples of non-fouling coatings (or anti-fouling coatings) include, but are not limited to, zwitterionic coatings, hydrophilic polymer coatings (e.g. poly- and oligoethylene glycol, PEG and OEG), mono-, oligo- and polysaccharide-based coatings, protein-based coatings, or coatings that include a combination thereof.

The thickness of the non-fouling coating 410 generally varies and is not intended to be limited. In some embodiments, the thickness of the non-fouling coating 410 of the sensor 400 is in a range from about 50 to about 1000 nm. In other embodiments, the thickness of the non-fouling coating 410 of the sensor 400 is in a range from about 400 to about 500 nm. Yet, in other embodiments, the thickness of the non-fouling coating 410 is not limited to the aforementioned thicknesses and can be tailored as desired. It is noted that the thickness of the non-fouling coating 410 shown in FIG. 4 is for representation purposes only and is not intended to drawn to scale.

After depositing the non-fouling coating 410 on the sensing surface 102, a bioabsorbable polymer layer 420 is deposited on the surface of the sensor 400. The bioabsorbable polymer layer 420 is disposed on top of the non-fouling coating 410, which protects both the non-fouling coating 410 and any exposed areas of the sensing surface 102. The composition and thickness of the bioabsorbable polymer layer 420 is described above with reference to FIG. 2.

The bioabsorbable polymer layer 420 can be sterilized and then implanted in a living animal as described above with reference to FIG. 3. The bioabsorbable polymer layer 420 protects the non-fouling coating 410 from the harsh conditions that the sensor 400 is subjected to during sterilization.

Figure 4B:
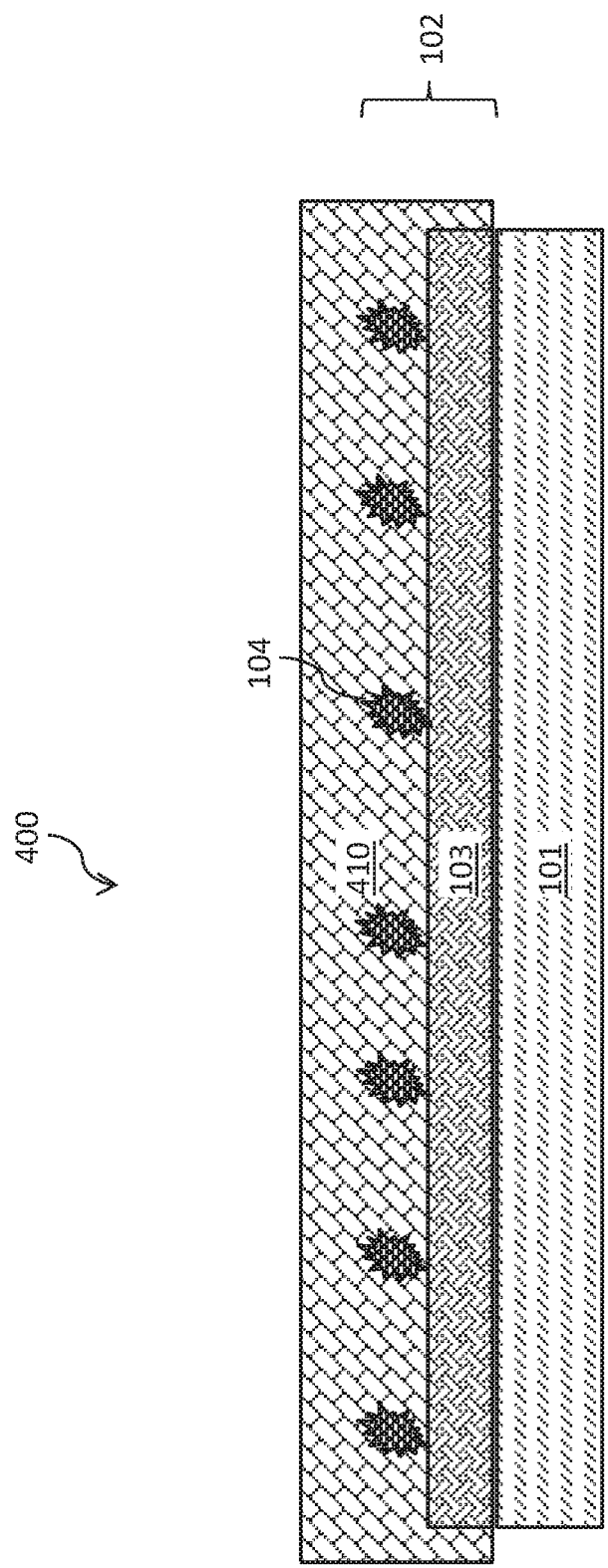
FIG. 4B is a cross-sectional side view of the controlled in-vivo sensor after implantation and removal of the bioabsorbable polymer layer.

After the sensor is then implanted into the living animal, the bioabsorbable polymer layer 420 will then dissolve or be removed from the surface of the sensor 400 to expose the non-fouling coating 420 and/or the sensing surface 102 after a known period of time, as shown in FIG. 4B.

Figure 5A:
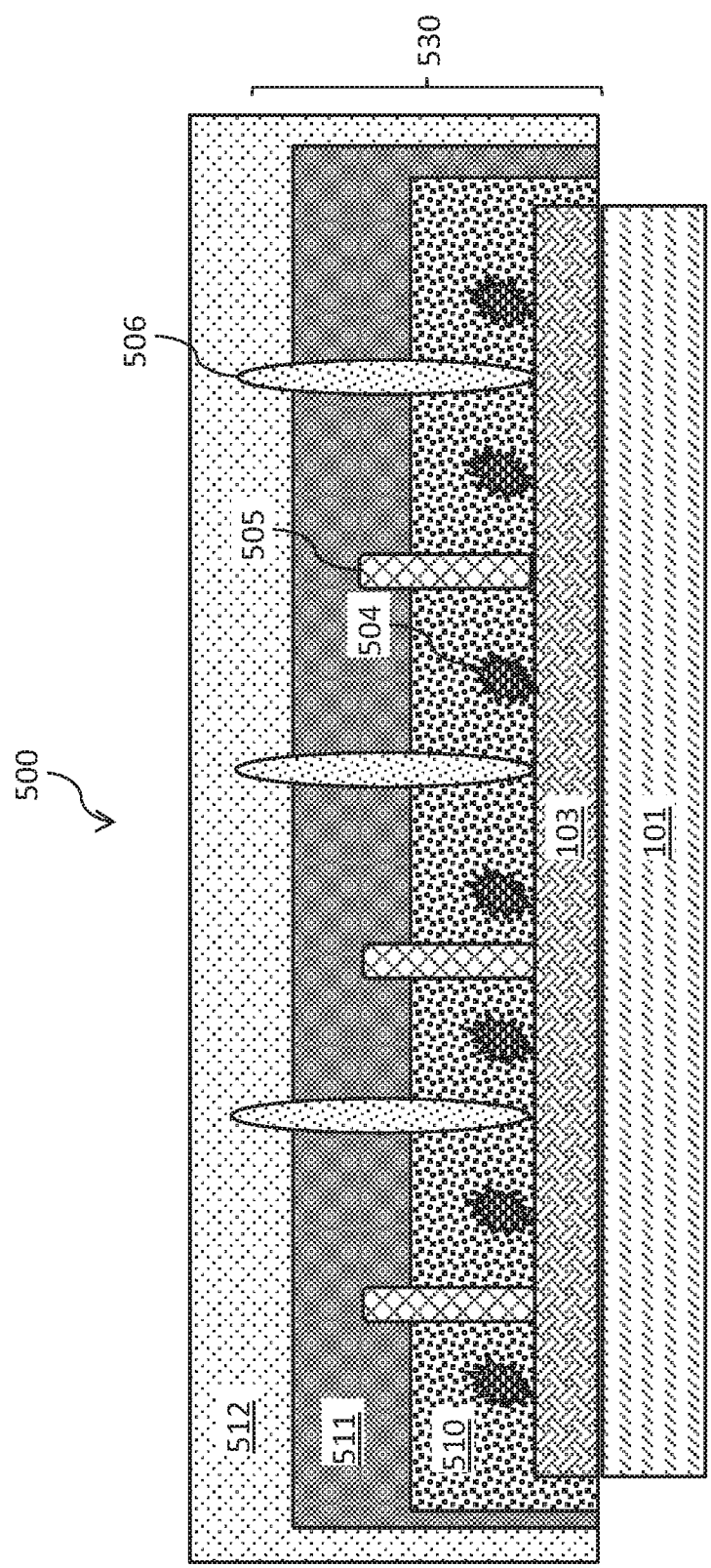
FIG. 5A is a cross-sectional side view of a controlled in-vivo sensor with several sensors according to embodiments.

FIG. 5A is a cross-sectional side view of a controlled in vivo sensor 500 according to embodiments. In-vivo sensor 500 includes a sensing surface 530 with several different sensors extending from the monolayer 103. The sensing surface 530 includes a first chemical moiety 504 (first sensor), a second chemical moiety 505 (second sensor), and third chemical moiety 506 (third sensor). Several layers of bioabsorbable polymers, or a thick layer of a single bioabsorbable polymer that covers all three sensors (first, second, and third sensors). Although first sensor, second sensor, and third sensor are shown as being arranged across the entire substrate, each sensor can be arranged side-by-side. Each sensor can have different thicknesses and/or compositions such that the sensors are exposed at different times.

First bioabsorbable polymer layer 510 covers the first sensor (first chemical moiety 504). Second bioabsorbable polymer layer 511 covers the second sensor (second chemical moiety 505). Third bioabsorbable polymer layer 512 covers the third sensor 506 (third chemical moiety).

Figure 5B:
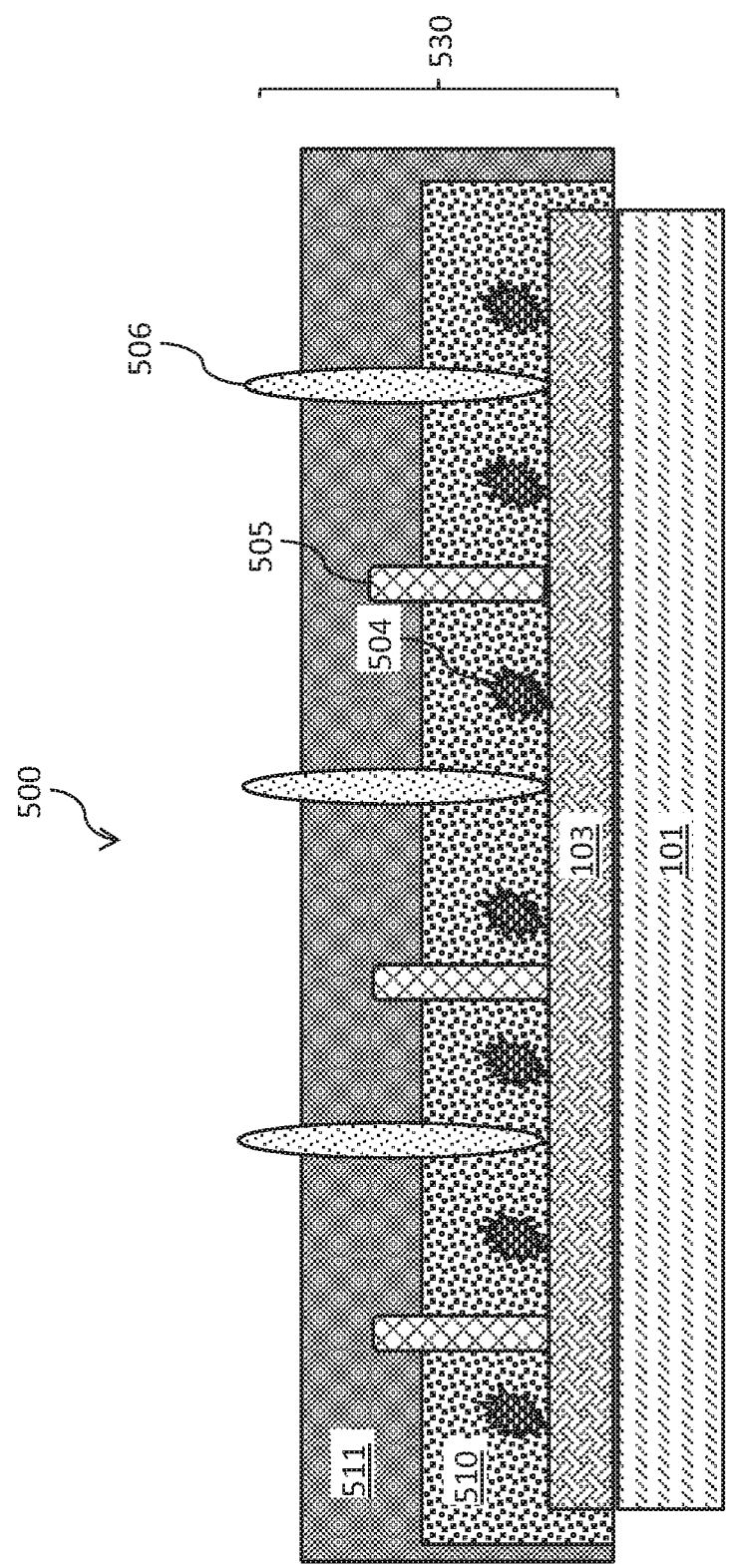
FIG. 5B is a cross-sectional side view of the controlled in-vivo sensor after implantation and removal of the upper bioabsorbable polymer layer.

After the sensor 500 is then implanted into the living animal, the upper bioabsorbable polymer layer (third bioabsorbable polymer layer 512) is removed over time, or dissolved to expose third sensor 506 of the sensing surface 530, as shown in FIG. 5B. Exposure of the third sensor occurs initially over a known period of time.

Figure 5C:
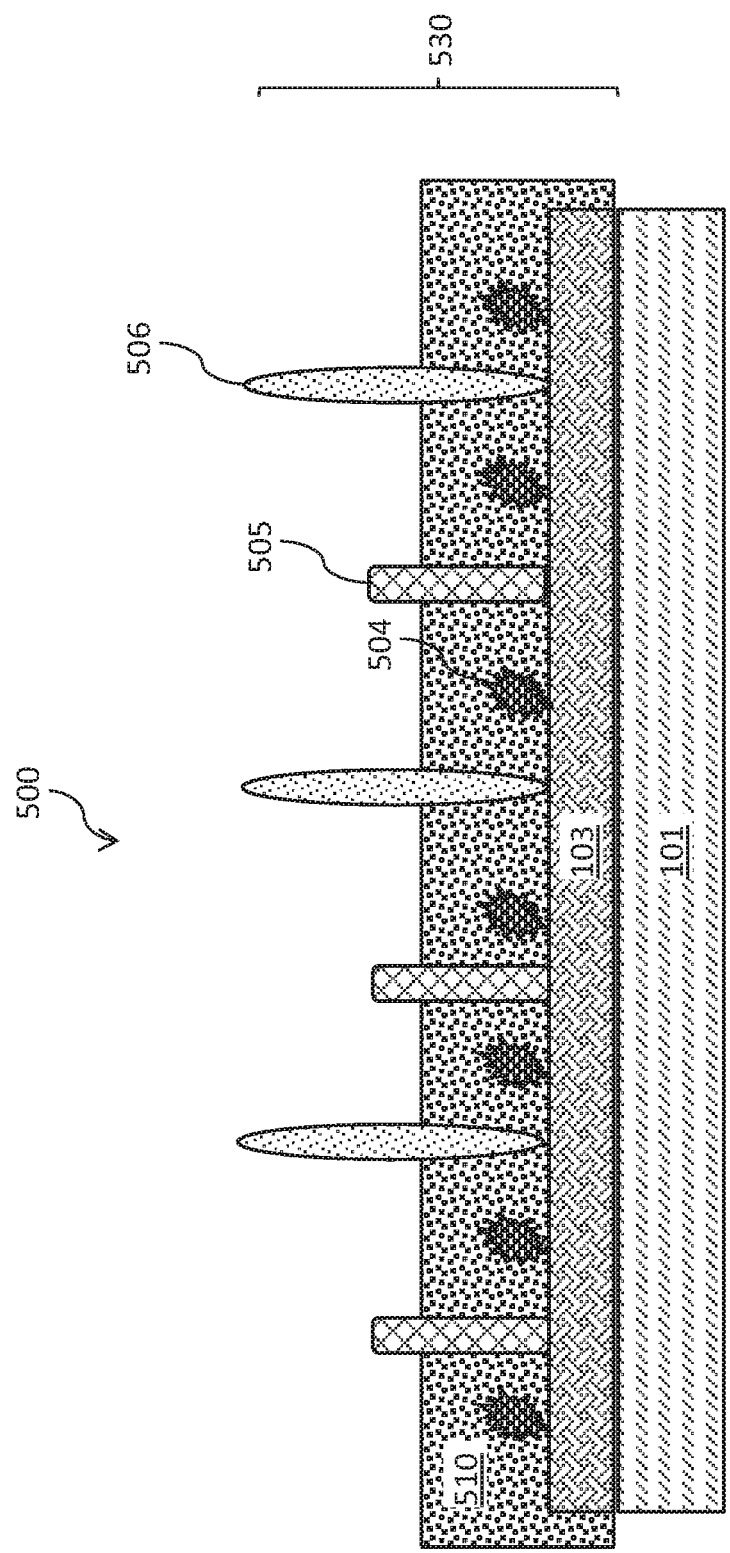
FIG. 5C is a cross-sectional side view of the controlled in-vivo sensor after implantation and removal of the middle bioabsorbable polymer layer.
Figure 5D:
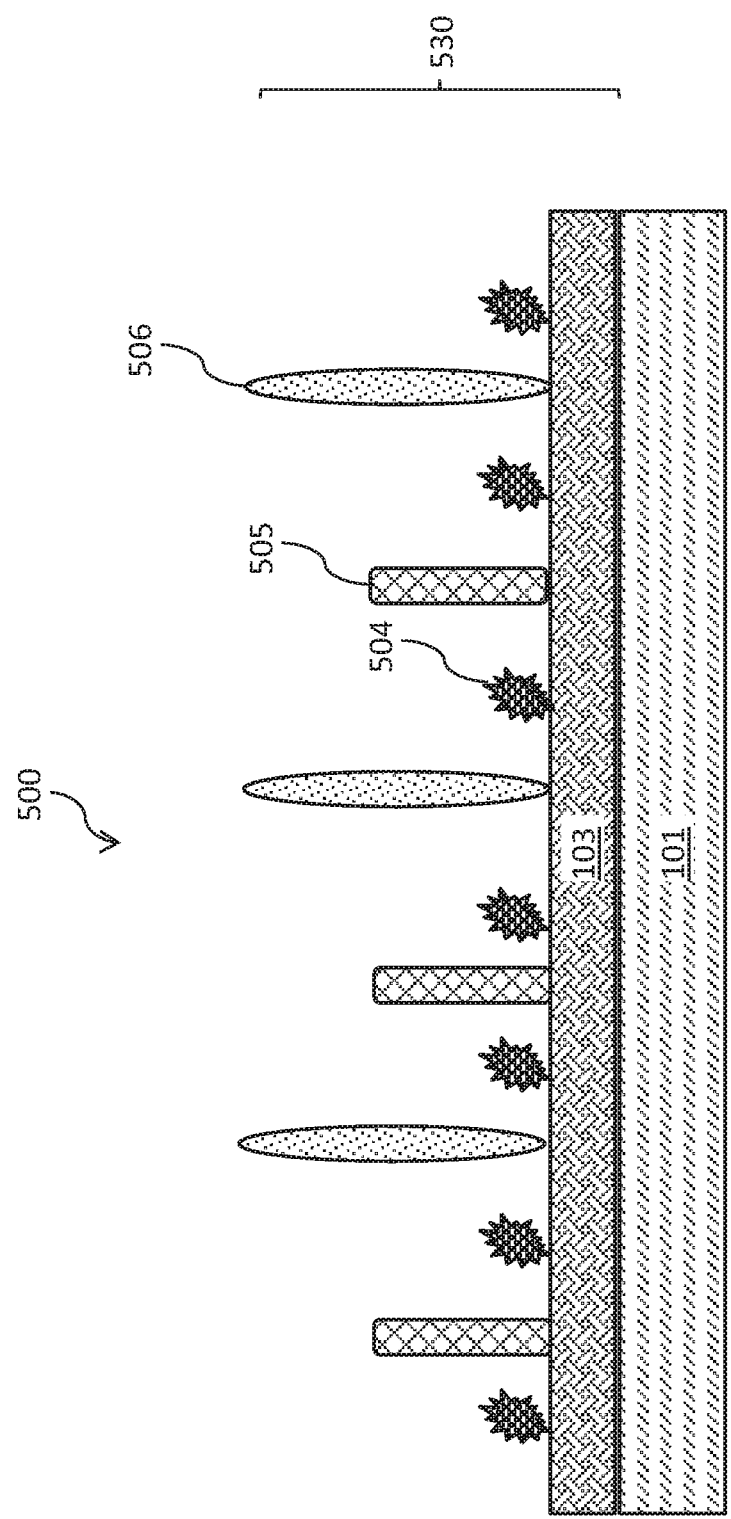
FIG. 5D is a cross-sectional side view of the controlled in-vivo sensor after implantation and removal of the bottom bioabsorbable polymer layer.

Then, after a longer period of time, the next/middle bioabsorbable polymer layer (second bioabsorbable polymer layer 511) is removed over time, or dissolved to expose second sensor 505 of the sensing surface 530, as shown in FIG. 5C.

Then, after an even longer period of time, the bottom/last bioabsorbable polymer layer (first bioabsorbable polymer layer 510) is removed over time, or dissolved to expose first sensor 504 of the sensing surface 530, as shown in FIG. 5C.

Thus, by staggering different sensors and bioabsorbable polymer layers on a single sensing surface, new and different sensors can be exposed over a staggered period of time. For example, different sensors can be exposed at, for example, day 1, day 7, day 14, day 21, etc. Such staggering allows for long-term monitoring in-vivo and mitigates the problem of sensor fouling. Although three sensors are shown in FIGS. 5A-5D, the controlled in-vivo sensors described herein can include any number of sensors and layers.

Although the compositions of the bioabsorbable polymer layers can be different in composition, in some embodiments first bioabsorbable polymer layer 510, second bioabsorbable polymer layer 511, and third bioabsorbable polymer layer 512 are the same polymeric composition. When the compositions are the same, different sensors are still exposed over a staggered period of time as the polymer layers desorb or dissolve to gradually expose the sensing surface.

Although not shown, additional non-fouling coatings can be included in the sensor 500. The non-fouling coatings are described above with reference to FIG. 4A and can be disposed beneath the bioabsorbable polymer layers.

Figure 6:
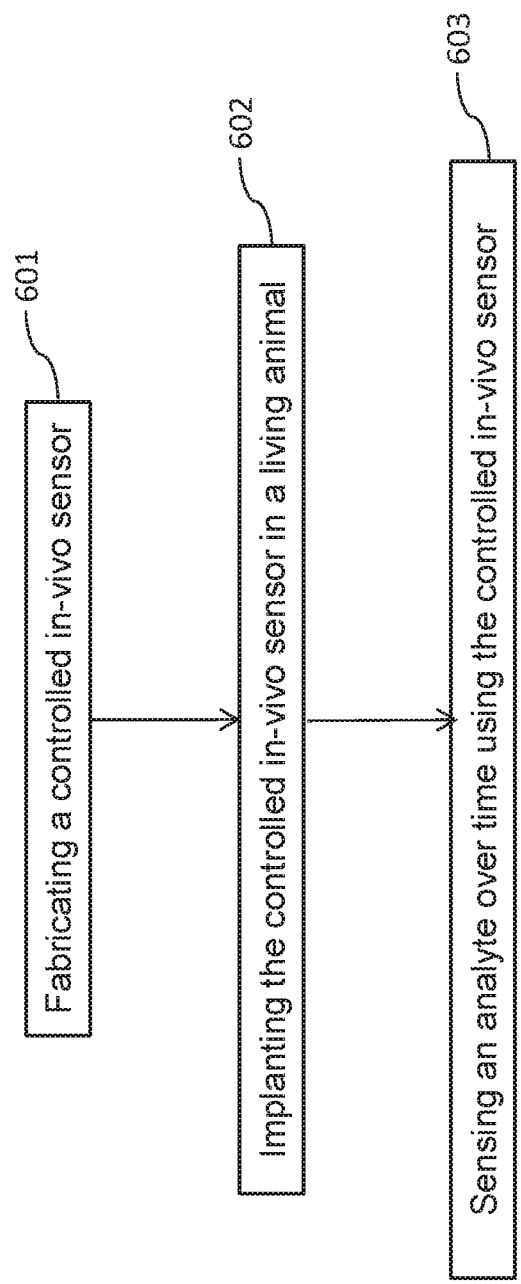
FIG. 6 illustrates a flow diagram of a method for controlled in vivo sensing according to embodiments.

FIG. 6 illustrates a flow diagram of a method for controlled in vivo sensing according to embodiments. In box 601, the method includes fabricating a controlled in-vivo sensor. Various in-vivo sensors are described above. In box 602, the method includes implanting the controlled in-vivo sensor in a living animal. In box 603, the method includes sensing an analyte of interest over time using the controlled in-vivo sensor.

Figure 7:
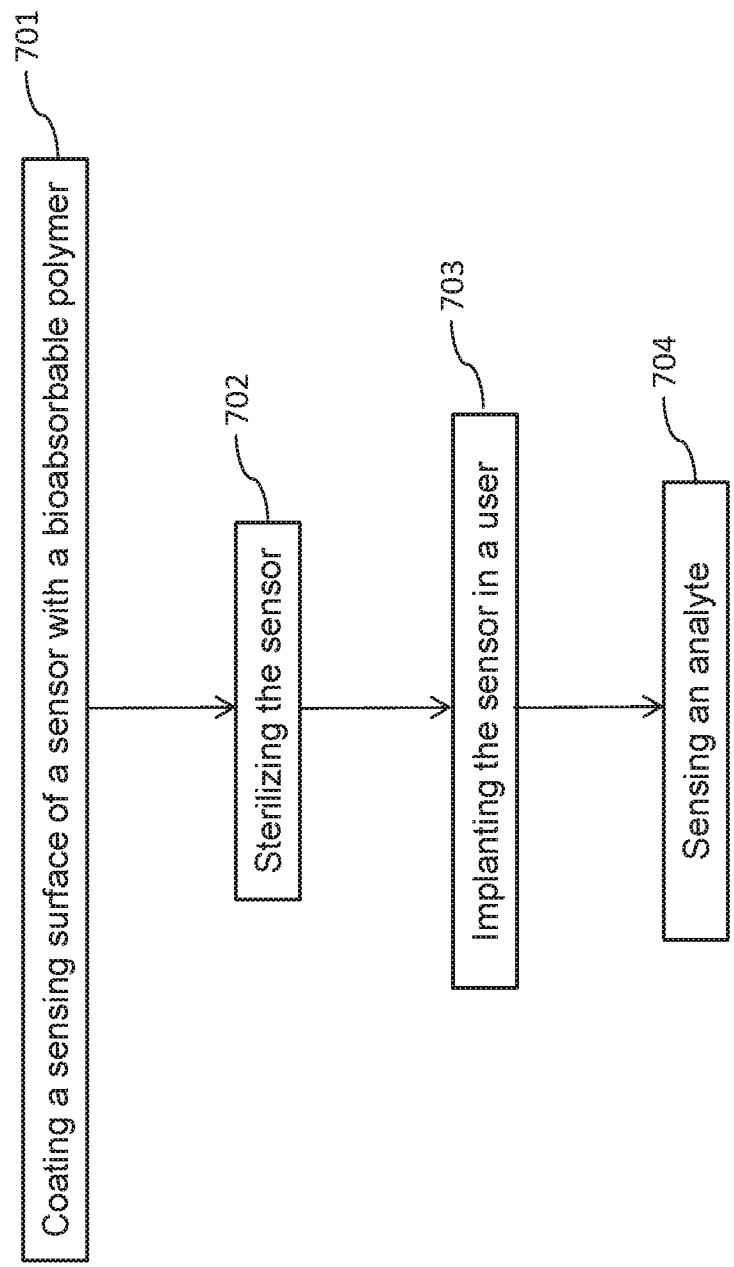
FIG. 7 is a flow diagram of a method for controlled in vivo sensing according to embodiments.

FIG. 7 is a flow diagram of a method for controlled in vivo sensing according to embodiments. In box 701, the method includes coating a sensing surface of a sensor with a bioabsorbable polymer. In box 702, the method includes sterilizing the sensor. In box 703, the method includes implanting the sensor in a living animal. In box 704, the method includes sensing an analyte.

Figure 8:
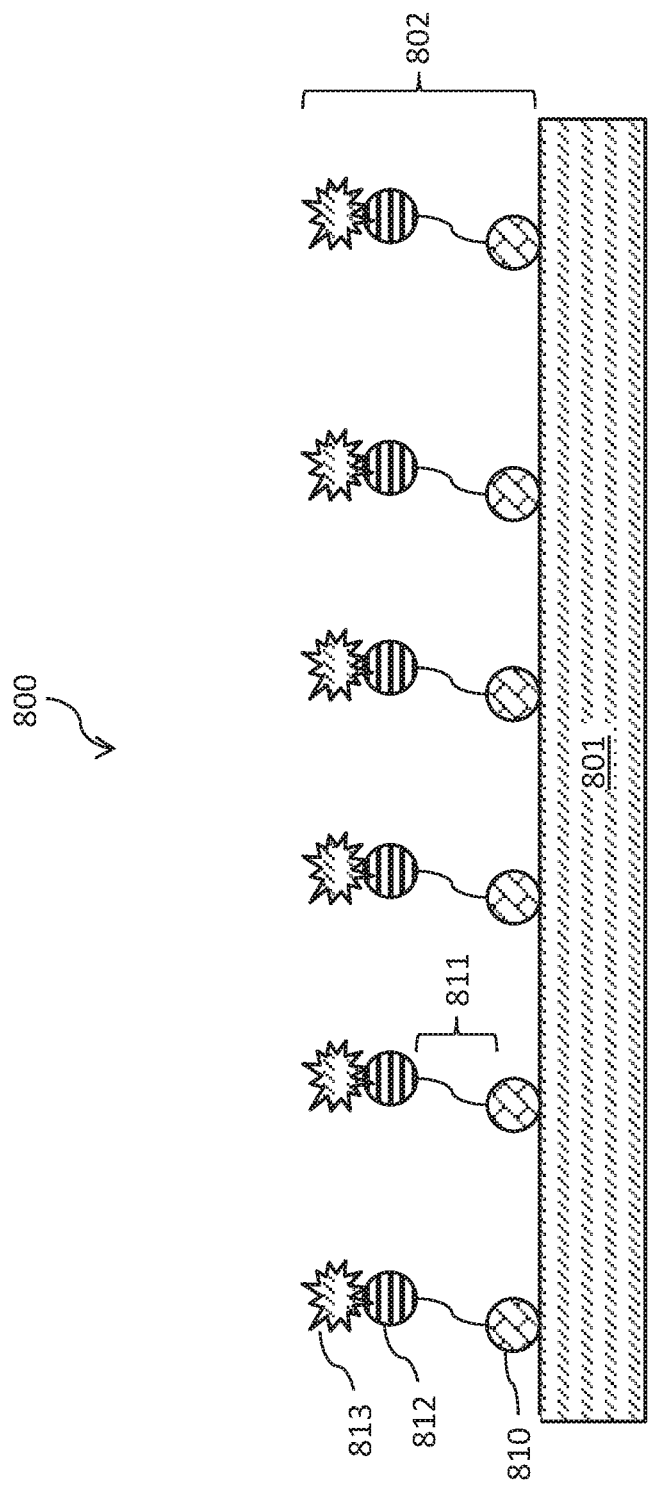
FIG. 8 is a cross-sectional side view of a controlled in-vivo sensor according to embodiments.

FIG. 8 is a cross-sectional side view of a controlled in-vivo sensor 800 according to embodiments. The sensor 800 includes a substrate 801 and a sensing surface 802. In an exemplary embodiment, the substrate 801 includes a metal film, such as a gold or silver film.

The sensing surface 802 includes an organic monolayer. The organic monolayer includes a polymer 811 extending from the surface of the substrate 801. The polymer 811 can be a copolymer. In exemplary embodiments, the polymer includes PEG.

The polymer 811 is bound to the surface of the substrate 801 via a first functional group 810. The first functional group 810 can be any chemical functional group that can interact with the substrate 801. For example, the first functional group 810 can be a thiol group when the substrate 801 is a gold film.

On the opposing end of the polymer 811 is a second functional group 812 that contacts or bonds to the chemical moiety 813 that will interact with or sense the analyte of interest once the sensor 800 is implanted. In exemplary embodiments, the chemical moiety is an antibody, such as IgG.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:
1. A method, comprising:
   forming a sensing surface on a surface of an in-vivo sensor, the sensing surface comprising a first sensor and a second sensor having different thicknesses and com- positions, the first sensor binding to a first analyte of interest, and the second sensor binding to a second analyte of interest;

coating the first sensor with a first bioabsorbable polymeric coating comprising a first bioabsorbable polymer, the first bioabsorbable polymeric coating covering and surrounding the first sensor and having a thickness in a range from about 50 to about 1,000 nanometers (nm);

coating the second sensor with a second bioabsorbable polymeric comprising a second bioabsorbable polymer, the second bioabsorbable polymeric coating covering and surrounding the second sensor and having a thickness in a range from about 50 to about 1,000 nm; and sterilizing the in-vivo sensor, at elevated temperature and high pressure, after coating the sensing surface with the bioabsorbable polymeric coating; and implanting the in-vivo sensor in an individual, the second bioabsorbable coating desorbing over time to expose the second sensor, and the first bioabsorbable coating desorbing subsequent to the second bioabsorbable coating to expose the first sensor.

2. The method of claim 1, wherein the first sensor or second sensor comprise an antibody.

3. The method of claim 1, wherein the first sensor and the second sensor are arranged side-by-side.

4. The method of claim 1, wherein the coating is spin-coating.

5. The method of claim 1, wherein the first bioabsorbable polymer or second bioabsorbable polymer is polylactic acid.

6. The method of claim 1, wherein the first bioabsorbable polymer or second bioabsorbable polymer is a cross-linking polymer.

7. The method of claim 1, wherein the surface of the sensor comprises a metal film.

8. The method of claim 1, wherein the second sensor comprises an antibody.

9. The method of claim 1, wherein the sensing surface comprises functionalized polyethylene glycol.

10. The method of claim 1, wherein the first bioabsorbable polymer or second bioabsorbable polymer comprises lactic acid, glycolic acid, glucose, polytrimethylene carbonate, collagen, laminin, hydroxyapatite, hyaluronan, amino acid, or a combination thereof.

11. The method of claim 1 further comprising disposing a non-fouling coating on the sensing surface.

* * * * *